United States Patent
Alexandrov et al.

(10) Patent No.: US 10,012,492 B2
(45) Date of Patent: Jul. 3, 2018

(54) NANO-SENSITIVE FOURIER-DOMAIN OPTICAL COHERENCE TOMOGRAPHY INSPECTION SYSTEM

(71) Applicant: NATIONAL UNIVERSITY OF IRELAND, GALWAY, Galway (IE)

(72) Inventors: Sergey Alexandrov, Galway (IE); Hrebesh Subhash, Galway (IE); Martin J. Leahy, Abbeyfeale (IE); Azhar Zam, Galway (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 51 days.

(21) Appl. No.: 15/027,056

(22) PCT Filed: Oct. 8, 2014

(86) PCT No.: PCT/EP2014/071536
§ 371 (c)(1),
(2) Date: Apr. 4, 2016

(87) PCT Pub. No.: WO2015/052232
PCT Pub. Date: Apr. 16, 2015

(65) Prior Publication Data
US 2016/0238370 A1 Aug. 18, 2016

(30) Foreign Application Priority Data
Oct. 11, 2013 (EP) .................................. 13188342

(51) Int. Cl.
*G01B 9/02* (2006.01)
*G01N 21/47* (2006.01)
(Continued)

(52) U.S. Cl.
CPC ........ *G01B 9/02044* (2013.01); *A61B 5/0066* (2013.01); *A61B 5/7257* (2013.01);
(Continued)

(58) Field of Classification Search
CPC ............ G01B 9/02091; G01B 9/02044; G01B 9/02083; G01B 9/02084; G01N 21/4795
See application file for complete search history.

(56) References Cited

U.S. PATENT DOCUMENTS 7,978,346 B1 * 7/2011 Riza ....................... G01B 11/24
356/368
2013/0301033 A1 * 11/2013 Alarousu .................. G01J 3/45
356/51
(Continued)

OTHER PUBLICATIONS

International Search Report issued in PCT/EP2014/071536; mailed Dec. 15, 2014.
(Continued)

*Primary Examiner* — Jonathan Hansen
(74) *Attorney, Agent, or Firm* — Studebaker & Brackett PC (57) ABSTRACT

An OCT imaging system (100) comprising a radiation emitter (SLD), a radiation receiver CCD), an interferometer (FC, PC, X-Scan, Y-Scan), a controller (COMP) which controls the emitter and processes received radiation data according to OCT to provide an output image. The controller (COMP) forms a spectrum of spatial frequencies along the depth direction. It calculates from the spectrum local spectra of spatial frequencies or periods along the depth direction for individual volume elements along the depth direction. It translates the local spectra of spatial frequencies or periods along the depth direction into the OCT image domain. It maps the local spectra into the volume elements to provide sensitivity on the nano-scale whereas the volume elements are in the micro-scale. The controller calculates information parameters from the translated and mapped local spectra. Thus the system (100) achieves nano-scale sensitivity although the volume elements are at the micro-scale.

18 Claims, 9 Drawing Sheets

(51) Int. Cl.
*A61B 5/00* (2006.01)
*G01N 21/17* (2006.01)

(52) U.S. Cl.
CPC ..... *G01B 9/02004* (2013.01); *G01B 9/02083* (2013.01); *G01B 9/02087* (2013.01); *G01B 9/02091* (2013.01); *G01N 21/4795* (2013.01); *G01N 2021/1787* (2013.01)

(56) References Cited

U.S. PATENT DOCUMENTS

2014/0028974 A1* 1/2014 Tumlinson ............. A61B 3/102 351/206
2015/0285685 A1* 10/2015 Wax ...................... G01J 3/2823 356/456

OTHER PUBLICATIONS

Ji Yi et al.; "Can Oct be sensitive to nanoscale structural alterations in biological tissue?"; Optics Express; Apr. 8, 2013; pp. 9043-9059; vol. 21; No. 7.

Yann Cotte et al.; "Marker-free phase nanoscopy"; Nature Photonics; Advance Online Publication; Jan. 20, 2013; pp. 1-5; Macmillan Publishers Limited.

7engbo Wang et al.; "Optical virtual imaging at 50 nm lateral resolution with a white-light nanoscope"; Nature communications; Mar. 1, 2011; pp. 1-6; 2:218; Macmillan Publishers Limited.

Guillaume Maire et al.; "Experimental Demonstration of Quantitative Imaging beyond Abbe's Limit with Optical Diffraction Tomography"; Physical Review Letters; 2009; pp. 1-4; 102; 213905; the American Physical Society.

David Huang et al.; "Optical Coherence Tomography"; Science; Reports; Nov. 22, 1991; pp. 1178-1181; vol. 254.

Bergey a. Alexandrov et al.; "Spectral encoding of spatial frequency approach for characterization of nanoscale structures"; Applied Physics Letters; 2012; pp. 1-5; 101; 033702; American Institute of Physics.

Shikhar Uttam et al.; "Tomographic imaging via spectral encoding of spatial frequency"; Optics Express; Mar. 25, 2013; pp. 7488-7504; vol. 21; No. 6.

Joey Enfield et al.; "In vivo imaging of the microcirculation of the volar forearm using correlation mapping optical aoherence tomography (cmOCT)"; Biomedical Optics Express; May 1, 2011; pp. 1184-1193; Vol. 2; No. 5.

Tyler S. Ralston et al.; "Interferometric synthetic aperture microscopy"; Nature Physics; Advance Online Publication; Jan. 21, 2007; pp. 1-6; Nature Publishing Group.

Bergey a. Alexandrov et al.; "Real-time quantitative visualization of 3D structural information"; Optics Express; Apr. 9, 2012; pp. 9203-9214; vol. 20; No. 8.

Shikhar Uttam et al.; "Investigation of depth-resolved nanoscale structural changes in regulated cell proliferation and chromatin decondensation"; Biomedical Optics Express; Apr. 1, 2013; pp. 596-613; vol. 4; No. 4.

Written Opinion issued in PCT/EP2014/071536; dated Dec. 15, 2014.

* cited by examiner

NANO-SENSITIVE FOURIER-DOMAIN OPTICAL COHERENCE TOMOGRAPHY INSPECTION SYSTEM

INTRODUCTION

The invention relates to inspection of a variety of objects, including body tissue (also in vivo), cell cultures, materials for material science, and micro and nano electronics components, for example.

Most of the fundamental pathological processes in living tissues, including cancer, exhibit changes at the nanoscale level. Recently the diffraction resolution limit has been broken and optical nanoscale microscopy has led to creation of nanoscopic medicine. However, nanoscopy largely requires labelling, is limited to superficial 2D imaging, and is not in general suitable for in vivo applications. Furthermore, it is currently believed that in many cases 2D biology does not translate into the real 3D situation.

Optical coherence tomography (OCT) provides non-invasive, contactless, depth resolving imaging of the object's internal structure. OCT facilitates cellular-level structural and functional imaging of living animal and human tissue as well as micro level imaging of different materials, but the structural sensitivity and resolution are limited to the microscale.

One of the effective approaches for improving performance of the optical system is the computed imaging approach which was successfully applied to optical systems, including optical tomography, wide-field characterisation of microstructure beyond the diffraction limit of the optical imaging system, and OCT. Light scattering spectroscopy (LSS) was incorporated in OCT for depth resolved nuclear morphology measurements. Spectroscopic information was extracted from OCT data and molecular imaging was realized. Correlation mapping optical coherence tomography (cmOCT) has been developed recently [8] to enable mapping of vasculature networks. Interferometric synthetic aperture microscopy (ISAM) has been developed to improve the out-of-focal plane resolution [9].

A spectral encoding of spatial frequency (SESF) approach for quantitative characterization of the structure with nanoscale sensitivity has been developed recently ([6], [7]). The ability to map axial structural information into each pixel of 2D image with nanoscale sensitivity has been demonstrated and application of this approach to 3D microscopic imaging has been discussed. In spite of the fact that ability of existing approaches to probe structure at micro and nanoscale have been shown, the depth resolved probing of 3D structure of scattering objects with nanoscale sensitivity remains a problem.

Recently the application of phase OCT to vibration measurements in the ear at the nanoscale has been demonstrated, and the ability of OCT to sense nanoscale structural alteration in weakly scattering media has been discussed [1]. The limitation to weakly scattering media generally excludes application to human tissue and to many materials of interest.

[10] describes visualization of the dominant structure (which corresponds to just one spatial frequency in depth direction) for each pixel of 2D image as a corresponding colour. [11] describes a different technique, quantitative phase microscopy (QPM). This technique works for semi-transparent objects, like cells, and cannot be applied to highly scattering media, like skin in vivo.

The invention is directed towards achieving improved sensitivity of 3D imaging for medical diagnostics, material science, nanofabrication, microelectronics.

REFERENCES

1. Yi, J. et al. "Can OCT be sensitive to nanoscale structural alterations in biological tissue?" Opt. Express 21, 9043-9059 (2013).
2. Cotte, Y. et al. "Marker-free phase nanoscopy. Nature Photon" 7, 113-117, (2013).
3. Wang, Z. et al. "Optical virtual imaging at 50 nm lateral resolution with a white light nanoscope" Nat. Commun. 2, doi:10.1038 (2011).
4. Guillaume, M., et al. "Experimental Demonstration of Quantitative Imaging beyond Abbe's Limit with Optical Diffraction Tomography" Phys. Rev. Lett. 102, 213905 (2009).
5. Huang, D. et al. "Optical Coherence Tomography" Science 254, 1178-1181 (1991).
6. Alexandrov, S. A., Uttam, S., Bista, R. K., Staton, K. & Liu, Y. "Spectral encoding of spatial frequency approach for characterization of nanoscale structures" Appl Phys Lett 101, 033702 (2012).
7. Uttam, S., Alexandrov, S. A., Bista, R. K. & Liu, Y. "Tomographic imaging via spectral encoding of spatial frequency" Opt. Express 21, 7488-7504 (2013).
8. [8] J. Enfield, E. Jonathan, and M. Leahy, "In vivo imaging of the microcirculation of the volar forearm using correlation mapping optical coherence tomography (cmOCT)," Biomedical Optics Express, vol. 2, pp. 1184-1193, May 1, 2011.
9. [9] T. S. Ralston, D. L. Marks, P. S. Carney, and S. A. Boppart, "Interferometric synthetic aperture microscopy," Nature Physics, vol. 3, pp. 129-134, February 2007.).
10. Sergey, A et al: "Real-time quantitative visualisation of 3D structural information", Optics Express, 9 Apr. 2012, vol. 20, No. 8, pages 9203-9214.
11. Shikhar Uttam et al: "Investigation of depth-resolved nanoscale structural changes in regulated cell proliferation and chromatin decondensation", Biomedical Optics Expess, 22 Mar. 2013, pages 596-613.

SUMMARY OF THE INVENTION

According to the invention, there is provided an OCT imaging method performed by an OCT system including a radiation emitter, a radiation receiver, an interferometer, and a controller adapted to control the emitter and to process received radiation data according to OCT to provide an output image, and the method comprising the steps of the controller:

a. forming a spectrum of spatial frequencies along the depth direction,
b. calculating from the spectrum of step (a) local spectra of spatial frequencies or periods along the depth direction for individual volume elements,
c. translating the local spectra of spatial frequencies or periods of step (b) into the OCT image domain,
d. mapping said local spectra into the volume elements to provide a sensitivity on a scale smaller by at least one order of magnitude than that of the volume elements, and
e. calculating information parameters from the translated and mapped local spectra of steps (c) and (d).

In one embodiment, the controller is adapted to also perform the step (b1) of forming an OCT image from the spectrum of step (a). In one embodiment, the spectrum of step (a) is a full complex spectrum.

In one embodiment, in step (c) the local spectra have a sensitivity which is higher by a plurality of orders of magnitude.

In one embodiment, in step (c) the local spectra have a sensitivity which is in the nano-scale whereas the volume elements are in the micro-scale or larger.

In one embodiment, the spectrum is formed by quasi-collimated radiation.

In one embodiment, the spectrum is formed by spectral domain OCT (SDOCT).

In one embodiment, the spectrum is formed by swept source OCT.

In one embodiment, the step (c) includes dividing the spectrum of axial spatial frequencies into zones, performing reconstruction of depth profile for each zone, and measuring signals at each point in each reconstructed depth profile.

In one embodiment, each zone corresponds to a narrow bandwidth of spatial frequencies and is considered as a single spatial frequency.

In one embodiment, reconstruction of corresponding images (axial Z (depth)-profiles) for each zone is performed via an inverse Fourier transform.

In one embodiment, step (d) includes mapping spectra of spatial frequencies into each pixel of each of a number of 2D images from step (b1).

In one embodiment, the controller selects the informative parameters to be calculated in step (e) according to a required application.

In one embodiment, the potential parameters include one or more of maximum spatial frequency, dominant spatial period, centre of mass, medium spatial frequency and medium spatial period, correlation between axial spectra.

In one embodiment, the magnitude of at least some calculated informative parameters is matched to colour of each pixel of 2D or each voxel of a 3D OCT image.

In one embodiment, a sequence of OCT images in time is recorded.

In one embodiment, local spectra of axial spatial frequencies or periods are reconstructed and analysed in time.

In one embodiment, time dependences of calculated informative parameters for each pixel of 2D or each voxel of 3D OCT image are calculated and plotted.

In one embodiment, the radiation receiver is a 2D detector and the spectral interferograms are formed simultaneously for all image points.

In another aspect, the invention provides an OCT system comprising a radiation emitter, a radiation detector, an interferometer, and a controller adapted to perform the steps of a method s defined above in any embodiment.

BRIEF DESCRIPTION OF THE DRAWINGS

The invention will be more clearly understood from the following description of some embodiments thereof, given by way of example only with reference to the accompanying drawings in which:—

DETAILED DESCRIPTION OF THE INVENTION

Description of the Embodiments

An OCT imaging system comprising a radiation emitter, a radiation receiver, a controller which controls the emitter and processes received radiation data according to OCT to provide an output image. The controller forms a spectrum of spatial frequencies along the depth direction. It calculates from the spectrum local spectra of spatial frequencies or periods along the depth direction for individual volume elements along the depth direction. It translates the local spectra of spatial frequencies or periods along the depth direction into the OCT image domain. It maps the local spectra into the volume elements to provide a sensitivity on the nano-scale whereas the volume elements are in the micro-scale. The controller calculates information parameters from the translated and mapped local spectra. Thus the system achieves nano-scale sensitivity although the volume elements are at the micro-scale.

The invention achieves nano-scale sensitivity OCT to structural changes, termed nano-scale sensitivity OCT ("nsOCT"). The OCT signal is formed by light scattered from high axial spatial frequency components of the object's scattering potential which correspond to submicron structure. The axial Fourier spectrum of the object's scattering potential is very informative and highly sensitive to structural changes because the optical system, if the required spectral transmission is provided, does not impose any limitations on the bandwidth of translated axial spatial frequencies. The range of axial spatial frequencies is limited by spectral bandwidth and the resolution of spatial frequencies is limited by spectral resolution. In conventional OCT, during the inverse Fourier transform to reconstruct axial profile, the spatial information is integrated and, as a result, the resolution and sensitivity even for the best OCT systems are relatively poor. In the invention, in addition to reconstruction of the conventional OCT image, the local axial Fourier spectra (profiles of the axial spatial periods) are directly translated into each voxel of the 3D OCT image. As a result, submicron structure can be visualized and nanoscale structural alterations within each voxel can be detected. Different informative parameters can be extracted from the local profiles of the axial spatial periods to characterize structure, depending on application, and mapped into the OCT image to form a colour map. For example, one of such parameters can be the maximum spatial frequency (period), which is the frequency at the maximal signal, which is directly related to the dominant size of the local structure.

The following sets out the major steps in various embodiments.

1. Form a conventional OCT image using Fourier domain OCT. An OCT apparatus such as illustrated n FIG. 6 may be used, in which "SLD" is the light source, "CCD" is a charge coupled device, "PC" is polarization controller, "FC" is fibre coupler, "OC" is optical circulator, "DG" is diffraction grating, "L1-LF" are lenses, the X and Y scanners are "X-Scan" and "Y-Scan", and the processing computer is COMP. The apparatus is conventional in the optical arrangement, however the image processing performed by the computer COMP is very different. Other types of known OCT apparatus may be used in the invention. A broad spectrum (short coherence length) or swept light source is used to access wide bandwidth of spatial frequencies. By collecting a spectral interference signal from the back scattering signal and the reference signal the depth profile of the object (A-scan) can be reconstructed. Moving in X and Y will permit 2D (B-Scan) and 3D (C-Scan) images to be formed.
2. Rescale collected spectrum in spatial frequencies (periods).
3. Divide spectrum into zones.
4. Reconstruct corresponding images (Z (depth)-profiles for each zone, each zone corresponds to one (or some limited bandwidth) spatial frequency).
5. Measure signal at each Z-coordinate in each profile, reconstructed for each zone, and reconstruct spectra of spatial frequencies (local axial Fourier transforms of the object) for each point in Z-profile.
6. Repeat operations 2-5 for all axial scans (A-scans). Other version instead of 5, 6 could be: (5) Repeat operations 2-5 for all axial scans (A-scans); (6) Measure signal at each Z, X-coordinates (where X is lateral coordinate) in each image, reconstructed for each zone, and reconstruct spectra of spatial frequencies (local axial Fourier transforms of the object) for each point in the image.
7. Map spectra of spatial frequencies (or periods) into each voxel of the 3D OCT image (or into each pixel of the cross sectional 2D images and en face 2D images).
8. Calculate corresponding informative parameters from the spectra of spatial frequencies depending on required specific application (for example, maximum in spatial frequency or period profile, centre of mass, correlation coefficients, etc.).
9. Match the magnitude of the selected informative parameter to corresponding colour and form colour nsOCT image where each voxel of the 3D image (or each pixel of the cross sectional 2D images and en face 2D images) will have colour which corresponds to magnitude of the selected informative parameter (for example, maximal spatial period in the Fourier spectrum). Put corresponding colour bar in the image.
10. Monitor structural changes with nanoscale sensitivity in space or in time.

It will be appreciated that this achieves nm scale sensitivity although not nm scale resolution. The spatial dimensions of the voxels are still in the μm scale, for example 50 μm×50 μm×50 μm. However within such voxel sizes the system can identify dominant structures at nm scale sensitivity.

EXAMPLES

Figure 6:
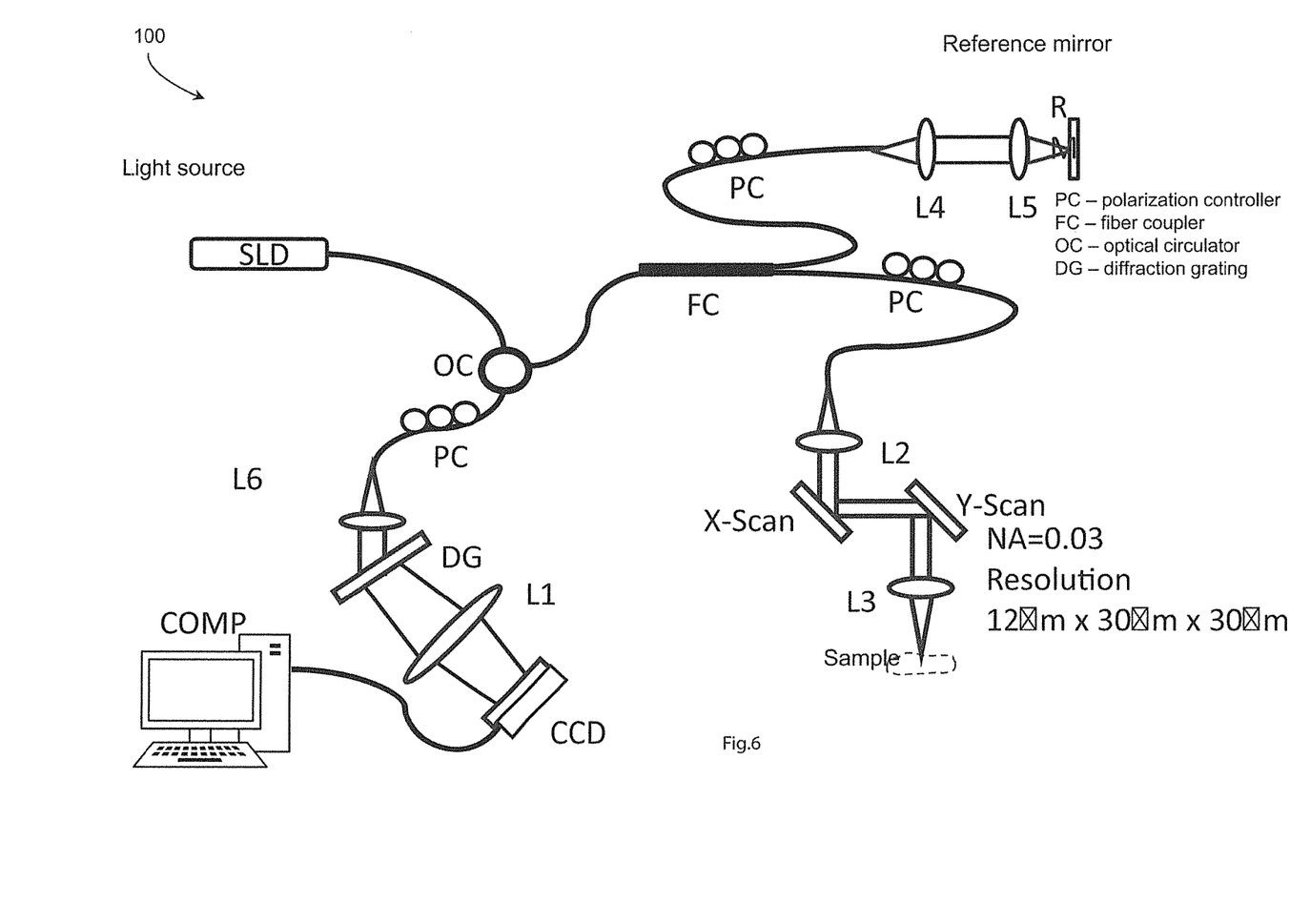
FIG. 6 is a diagram of an OCT apparatus used for presented examples.

To experimentally demonstrate the capabilities of the invention we used a spectral domain OCT (SD-OCT) setup such as that of FIG. 6 with low NA optics (see Methods) was used. The voxel size in OCT images was 12 μm×30 μm×30 μm, the spatial interval to reconstruct profiles of the axial spatial periods was 4 nm and the voxel size was 50 μm×30 μm×30 μm.

First of all, to experimentally demonstrate the ability of our approach to probe the axial structure within a highly scattering 3D object with nano-scale sensitivity we used a sample which consists of two layers of self-assembled nanosphere aggregates of nanospheres of known sizes (see Methods). Such a sample produces a highly scattering 3D quasi-periodic structure in which the spatial periods depend on nanosphere size and packing, while also introduces some complexity and can serve as a surrogate tissue phantom. The coefficient of variance (CV) for both sizes was ≤3% (see Methods), so there was some probability that nanospheres from different layers could have the same diameters.

Figure 1:
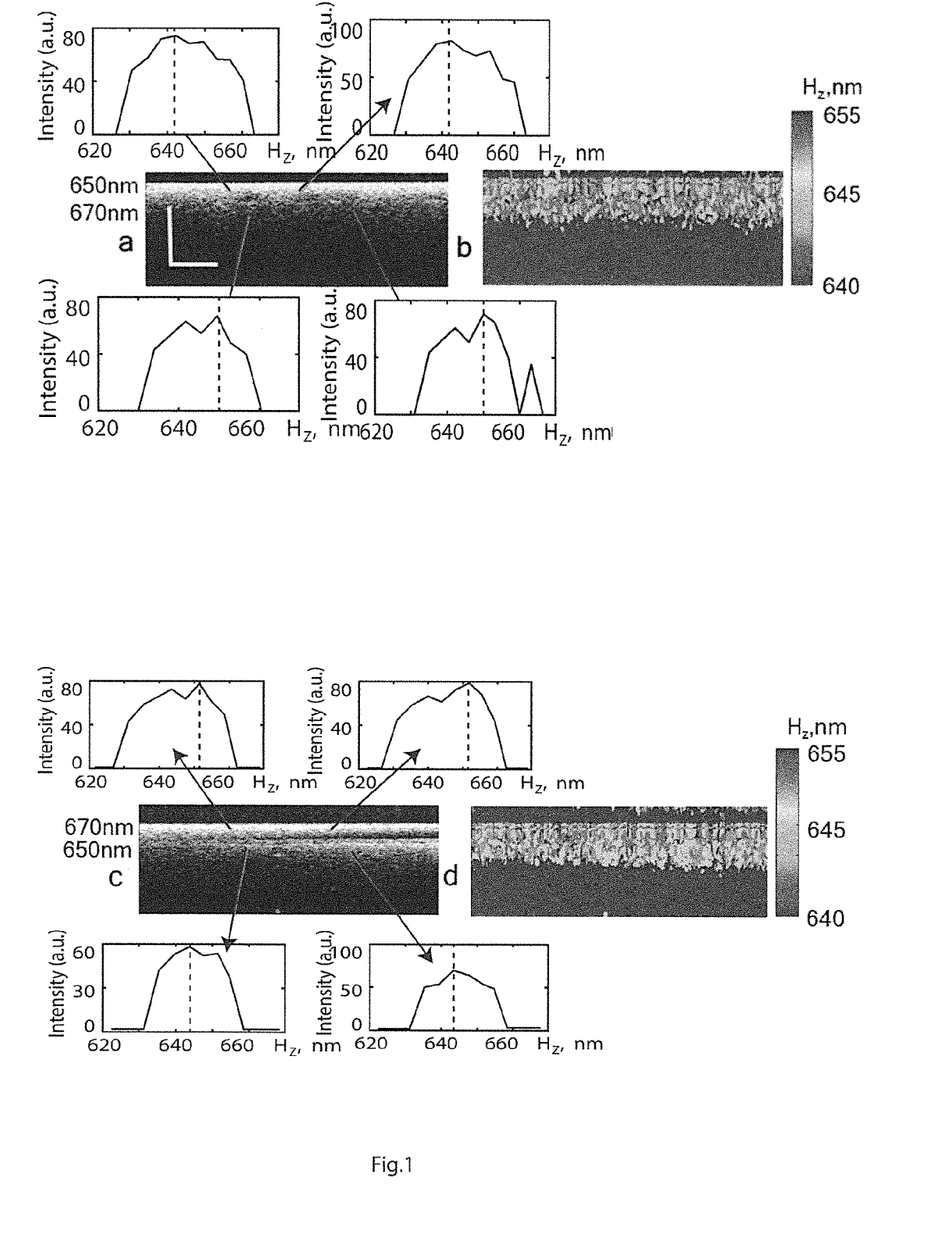
FIG. 1 shows output images for inspection by a system of the invention of two layers of nanospheres of 650 nm and 670 nm sizes, in which a and c are conventional OCT images with profiles of the axial spatial periods for selected locations, and b and d are "nsOCT" images provided by a system of the invention, and in which the lateral and depth scale bars are 500 μm.

In FIGS. 1*a*, 1*b* the top layer contains nanospheres with 650 nm mean diameter and the bottom layer—with 670 nm mean diameter. These layers of nanosphere aggregates, whose sizes are well beyond the resolution limit of the OCT system, are indistinguishable in the conventional OCT image FIG. 1*a* and, of course, the difference between them of 20 nm cannot be detected. But the nsOCT approach shows that in most points in the bottom layer, the maximum of the profiles of the axial spatial periods was shifted to larger values (larger dominant sizes of the structure) relative to corresponding profiles in the top layer.

FIG. 1*a* shows the plot of two of these selected points for the bottom and top layers, respectively.

In FIG. 1*b* the nsOCT image as a map of the maximal axial spatial periods (dominant axial structure sizes) is shown. One can see that for most locations the sizes of dominant axial structure in bottom layer are shifted to larger values than in the top layer and it is possible to clearly distinguish two layers with different nanostructures. In FIG. 1*c, d* the same results are presented when the layers were flipped. These results demonstrate that the spatial difference in structural size as small as 20 nm can be detectable using the invention, nsOCT.

A second experiment demonstrates the ability of nsOCT to detect nanoscale structural changes in time. Structural changes less than 30 nm within the scattering sample were made as described in Methods. We recorded 50 B-scans before and 50 B-scans after structural changes were made. Images in FIG. 2 demonstrate that there are no detectable structural changes at selected locations between second (FIG. 2*a, e*) and last (FIG. 2*b, f*) frames before, as well as between second (FIG. 2*c, g*) and last (FIG. 2*d, h*) frames after structural changes were made. The profiles of the axial spatial periods (FIGS. 2*a, b* and *c, d*) and maximal (dominant) spatial periods in nsOCT images (FIGS. 2*e, f* and *g, h*), presented as colour maps, remain unchanged. The standard deviations of the maximal spatial periods for selected points were $10^{-13}$ nm and 1.18 nm before and $10^{-13}$ nm for both locations after structural changes.

Figure 2:
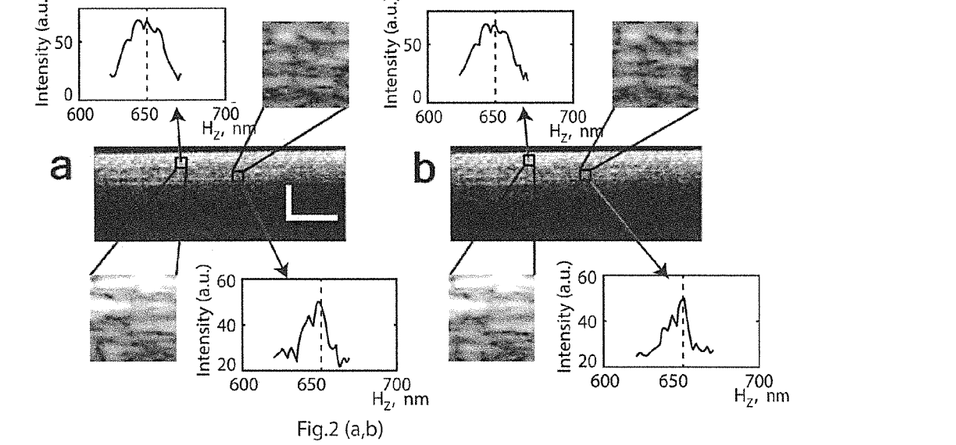
FIG. 2 shows OCT images of multilayer scattering tape with profiles of axial spatial periods and magnified portions for two selected locations (a-d) and "nsOCT" images with magnified portions for the same two selected locations (e-j) before (a, b, e, f) and after (c, d, g, h) top surface displacement of 30 nm, and in which images a, c and e, g are second frames, images b, d and f, h are fiftieth frames, images e, j are averaged images for 49 frames before e and after j top surface displacement, and lateral and depth scale bars are 500 μm.

It is impossible to get any information about nanostructural changes by comparison of conventional OCT images FIGS. 2a, b and c, d., but the structural changes can be clearly seen by comparison the profiles of the axial spatial periods, presented in OCT images FIGS. 2a, b and c, d and colour maps of dominant spatial periods in nsOCT images in FIG. 2e, f and FIG. 2g, h. The dominant spatial periods were decreased by 5.27 nm and 1.69 nm for two selected locations.

This experiment also confirms that nanoscale structural changes smaller than 30 nm can be detected using nsOCT.

In another experiment we demonstrate the ability of nsOCT to detect relatively fast structural changes, such as blood flow, within highly scattering media. We imaged Brownian motion within Intralipid in plastic tubes through a scattering medium. The time interval between images FIG. 3a, c and FIG. 3b, d was 20 ms. It can be seen that there are obvious changes in the profiles of the axial spatial periods for points within the tubes, but there are no visible changes for points outside the tubes. In magnified portions of the nsOCT images FIG. 3 c, d the structural changes within tubes are clearly seen.

Figure 3:
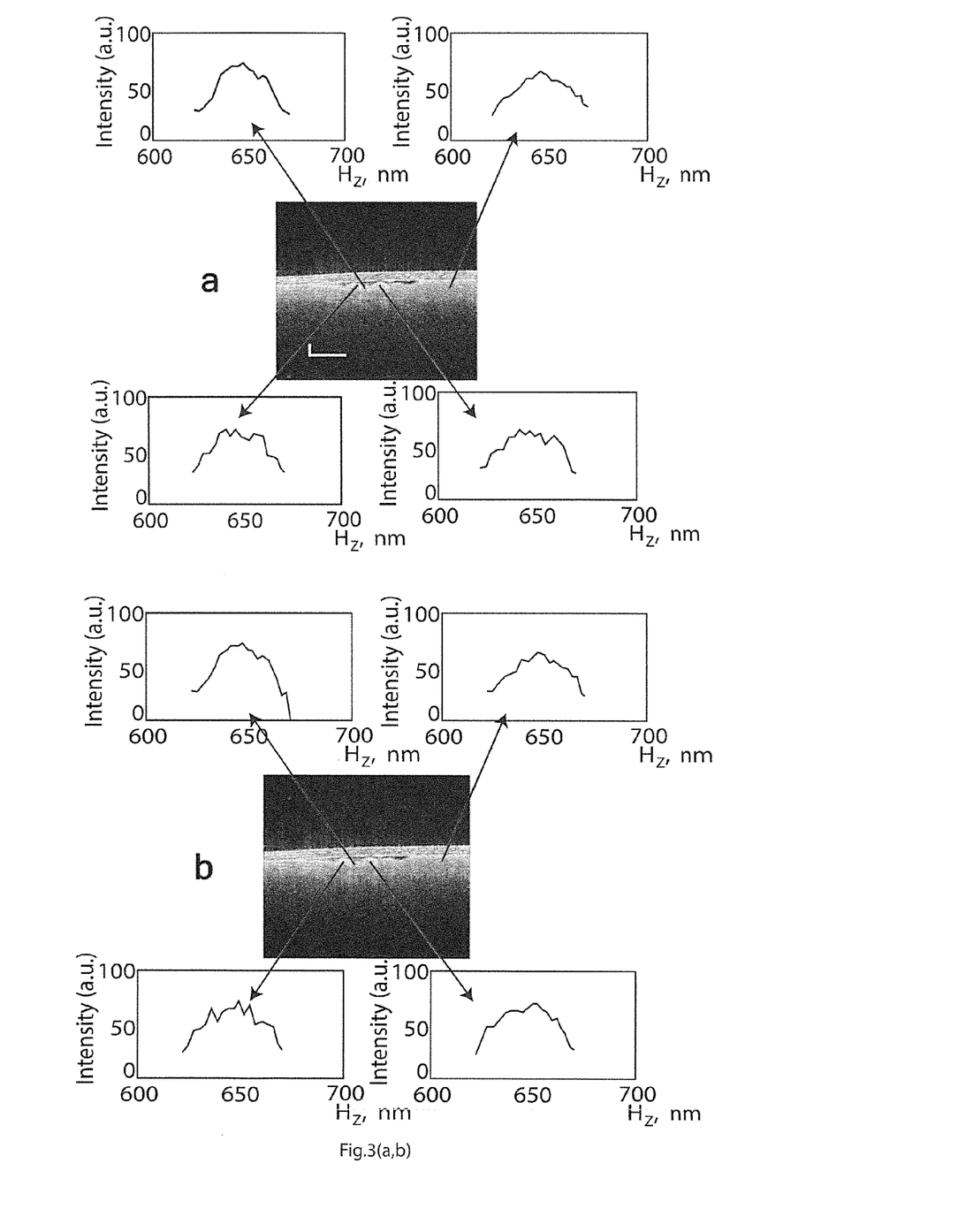
FIG. 3 shows conventional OCT (a, b) and "nsOCT" (c, d) images of Intralipid within two tubes, in which time interval between images (a, c) and (b, d) is 20 msec, and for two selected locations within the tubes and two locations outside the tubes the profiles of the axial spatial periods and magnified portions of nsOCT images are presented, and again lateral and depth scale bars are 500 μm.
Figure 4:
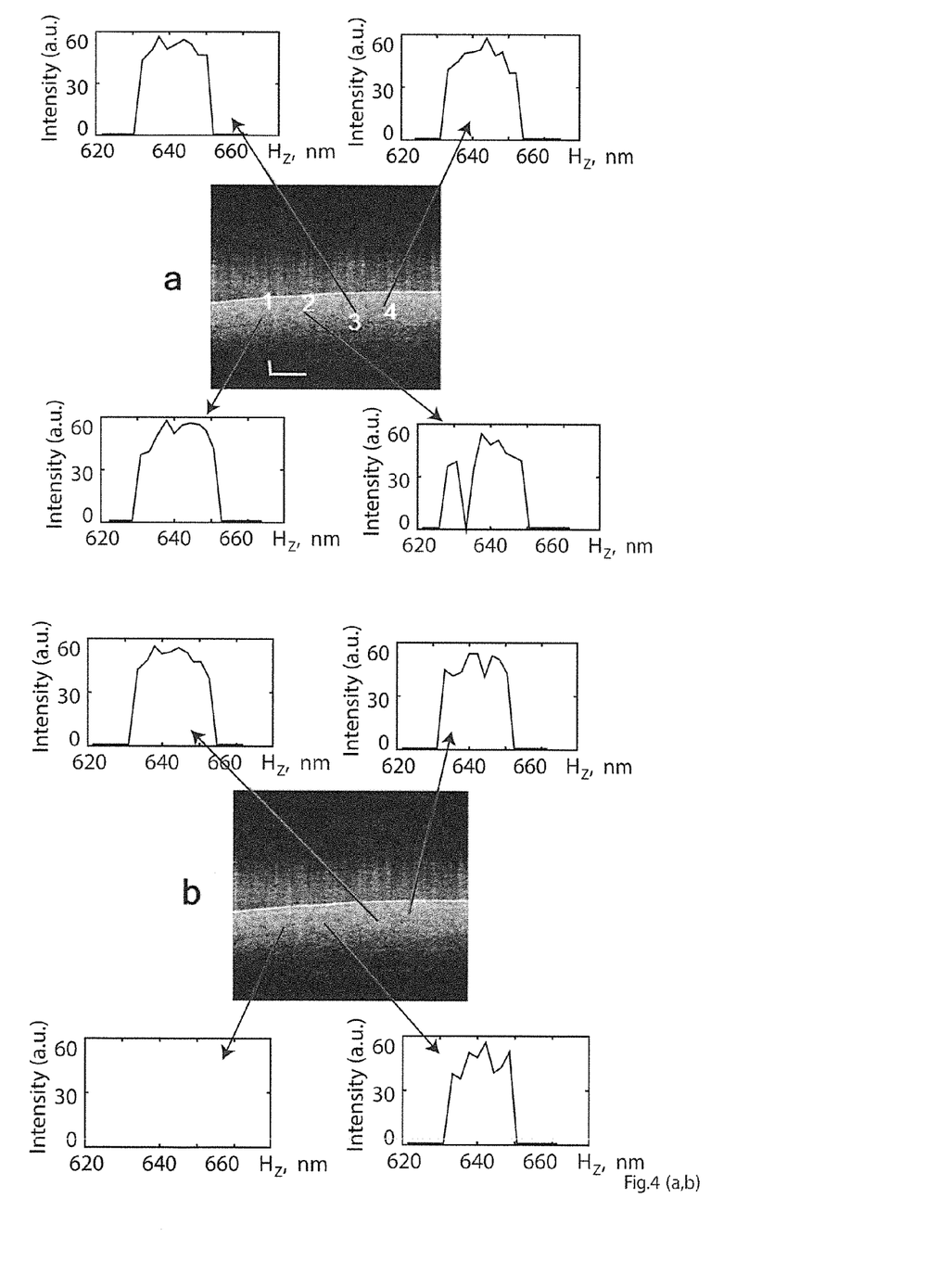
FIG. 4 shows conventional OCT (a, b) and "nsOCT" (c, d) in vivo images of a finger nail fold, in which the time interval between images (a, c) and (b, d) is 20 msec, and in which for four selected locations the profiles of the axial spatial periods and magnified portions of nsOCT images are presented, and in which lateral and depth scale bars are 500 μm.

Finally, in FIG. 4 an example of nsOCT application to in vivo imaging of human skin is presented. Within living tissue there are always nanoscale structural changes, but we found that in some areas within the finger nail fold the alterations in internal structure are faster than in other areas. The time interval between images FIG. 4a, c and FIG. 4b, d was 20 ms, the same as for our model experiment (FIG. 3). We can see the structural changes in the profiles of the axial spatial periods (FIG. 4 a, b) and in the magnified portions of the nsOCT images (FIG. 4 c, d) for points 2, 4 during this time interval, while in other areas (points 1, 3) the structure remains unchanged. The most likely reason for such structural changes is blood flow. The information about changes in axial spatial period profiles can be used for determination of the blood flow velocity.

Methods nsOCT setup was based on the SD-OCT setup shown in FIG. 6. A broadband 1310 nm superluminescent diode SLD with bandwidth of 83 nm (SLD, Dense Light, Singapore) was coupled into the interferometer, via an optical coupler OC. The spectrometer consisted of a 50 mm focal length collimator, a 1145 lines/mm transmitting grating, an achromatic lens with a 100 mm focal length and a 14-bit, 1024 pixels InGaAs line scan camera (SU1024LDH2, Goodrich Ltd. USA) with a maximum acquisition rate of 91 kHz. This spectrometer setup had a spectral resolution of 0.1432 nm, which gave a maximum imaging range of ~6 mm (in air). The sample arm consists of a pair of galvanometric driven mirrors and an objective lens with 50 mm diameter (NA=0.03) which provided a lateral resolution of ~30 µm. The measured sensitivity of the system was ~105 dB near the zero-delay line. The sensitivity drop off of the system was ~20 dB at a depth range±3 mm. The measured axial imaging resolution of the system was ~12 µm in air (~8.6 µm in human skin) and a lateral resolution was ~30 µm.

The OCT images were reconstructed for each small portion of axial spatial frequencies and the profiles of the axial spatial periods for each voxel were extracted from these images. nsOCT images were formed as maps of the maximal spatial periods for each voxel. The uncertainty in spatial periods determination for NA=0.03 was less than 1 nm. The voxel size in nsOCT images was 50 µm×30 µm×30 µm and spatial interval to reconstruct profiles of the axial spatial periods was 4 nm.

Nanoscale Structural Changes within the Sample.

Figure 5:
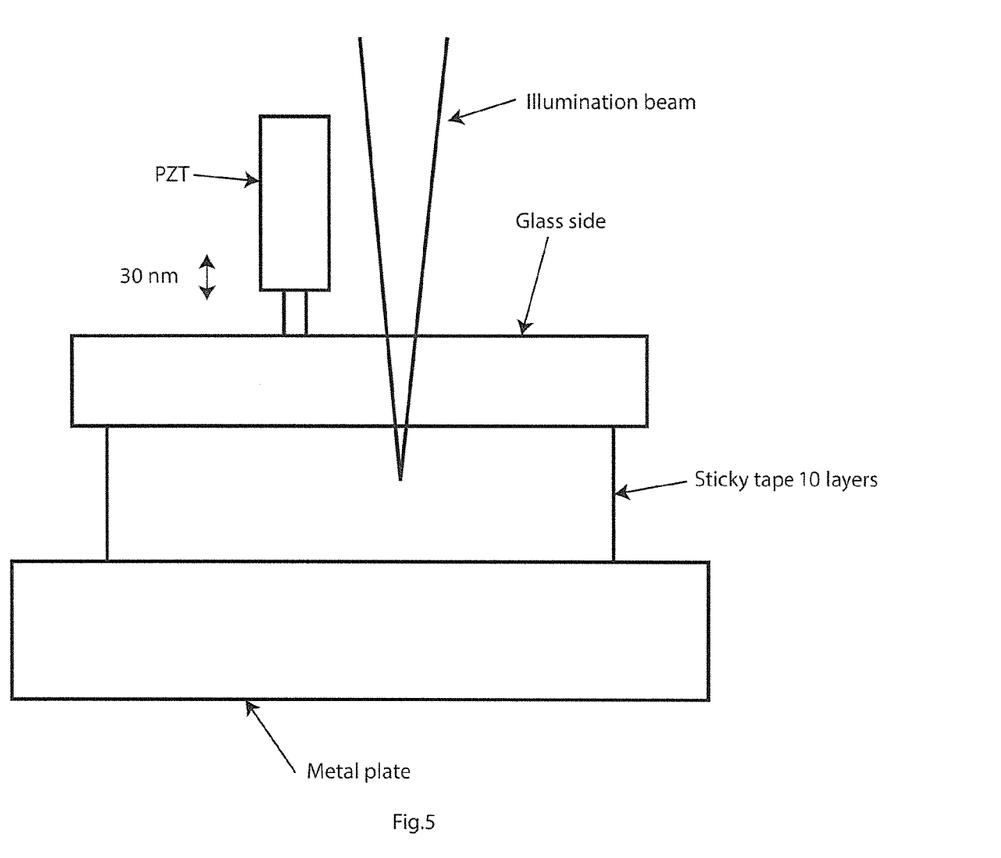
FIG. 5 is a diagram showing a test set-up with nanoscale tape so that nanoscale structural changes within the sample (multilayers of sticky tape) can be imaged Schematic of making nanoscale structural changes within the sample (multilayers of sticky tape)

The sample, which consists of ten layers of scattering sticky tape, was placed on the solid stable basis (metal plate), as shown in FIG. 5. Metal plate was rigorously fixed to the bench. On the top of the sample the glass slide was placed. This slide was shifted on 30 nm by PZT. So the top surface of the sample was shifted, but the bottom surface remained stable. As a result the structural changes which are smaller than 30 nm were introduced within the sample. The distance between low NA Illumination beam from OCT system and PZT tip was about 10 mm. Fifty OCT images (B-scans) were taken before and after 30 nm shift was applied.

Sample Preparation.

Samples with Nanospheres

An aliquot of diluted monodispersed polystyrene nanosphere suspension (Thermo Scientific) was uniformly smeared onto the glass slide and dried, forming a thick layer of nanosphere aggregates. Two such samples were prepared, first with nanospheres diameter 650 nm and second with nanospheres diameter 670 nm (CV≤3% according to manufacturer's specification, where CV is the Coefficient of Variation, one standard deviation expressed as a percentage of the peak diameter). The complex two layers sample was made as a sandwich of two such samples of single size nanospheres with coverslip between them.

To model blood flow we used two plastic tubes with internal diameter 300 microns, filled with 9% Intralipid. The tubes were fixed on the glass slide and covered with 7 layers of scattering tape.

For in vivo experiments we put a drop of glycerol on finger nail fold of a volunteer and captured OCT images.

The invention takes a very different approach from those described in the prior art. For example, referring to documents [10] and [11] these do not describe or suggest forming a depth resolved spectrum of spatial frequencies along the depth direction, calculating from the spectrum local spectra of spatial frequencies or periods along the depth direction for individual volume elements along the depth direction, and mapping the local spectra into the volume elements to provide a sensitivity on a scale smaller by at least one order of magnitude than that of the volume elements, and calculating information parameters from the translated and mapped local spectra.

Advantageously, the invention provides extracting the local spectra of spatial frequencies in the depth direction (depth profiles) and mapping them to each voxel of the 3D reconstructed image.

It will be appreciated that the invention achieves a very large improvement in sensitivity of OCT to structural changes. Improvement of more than 300 times has been demonstrated; using OCT system with resolution 12 µm×30 µm×30 µm we were able to detect the size difference between nanosphere aggregates as small as 20 nm and temporal structural changes within scattering samples less than 30 nm. The sensitivity is limited by the spectral resolution and can go far beyond what we have demonstrated here.

The invention is not limited to the embodiments described but may be varied in construction and detail.

The invention claimed is:

1. An OCT imaging method of an object having a structure, the OCT imaging method performed by an OCT system including a radiation emitter, a radiation receiver, an interferometer, and a controller adapted to control the emitter and to process received radiation data according to Fourier Domain OCT to provide an output image, and the method comprising the steps of the controller:

a. forming a spectrum of axial spatial frequencies along the depth direction of a spectral interference signal generated by a back scattering signal from the OCT system;
b. calculating from the spectrum of step (a) local axial spectra of spatial frequencies or periods along the depth direction for individual volume elements;
    b1. forming an OCT image from the spectrum of step (a);
c. translating said local axial spectra of spatial frequencies or periods of step (b) into the Fourier Domain OCT image domain;
d. mapping said local axial spectra into the volume elements to provide a sensitivity to structural changes of the object on a scale smaller than that of the volume elements; and
e. calculating information parameters from the translated and mapped local spectra of steps (c) and (d).

2. The method as claimed in claim 1, wherein the spectrum of step (a) is a full complex spectrum.

3. The method as claimed in claim 1, wherein in step (c) the local spectra have a sensitivity which is in the nano-scale whereas the volume elements are in the micro-scale or larger.

4. The method as claimed in claim 1, wherein the spectrum is formed by using quasi-collimated radiation for illumination.

5. The method as claimed in claim 1, wherein the spectrum is formed by spectral domain OCT (SDOCT).

6. The method as claimed in claim 1, wherein the spectrum is formed by swept source OCT (SSOCT).

7. The method as claimed in claim 1, wherein the step (c) includes decomposition of the spectrum of axial spatial frequencies into zones, performing reconstruction of an image depth profile for each zone, and measuring signals at each point in each reconstructed image depth profile.

8. The method as claimed in claim 1, wherein the step (c) includes decomposition of the spectrum of axial spatial frequencies into zones, performing reconstruction of image depth profile for each zone, and measuring signals at each point in each reconstructed image depth profile, and wherein each zone corresponds to a narrow bandwidth of spatial frequencies and is considered as a single spatial frequency.

9. The method as claimed in claim 1, wherein the step (c) includes decomposition of the spectrum of axial spatial frequencies into zones, performing reconstruction of image depth profile for each zone, and measuring signals at each point in each reconstructed image depth profile, and wherein reconstruction of corresponding images (axial z (depth)-profiles) for each zone is performed via an inverse Fourier transform.

10. The method as claimed in claim 1, wherein in step (c) the controller forms OCT 2D images, and wherein step (d) includes mapping spectra of spatial frequencies into each pixel of said 2D images.

11. The method as claimed in claim 1, wherein the controller selects the information parameters to be calculated in step (e) according to a required application.

12. The method as claimed in claim 1, wherein the controller selects the information parameters to be calculated in step (e) according to a required application, and wherein the information parameters include one or more of spatial frequency at maximum signal, dominant spatial period, center of mass, medium spatial frequency and medium spatial period, and correlation between axial spectra.

13. The method as claimed in claim 1, wherein in step (b) the controller forms 2D or 3D images, and wherein the magnitude of at least some calculated information parameters is mapped to color of each pixel of said 2D images or each voxel of said 3D OCT images.

14. The method as claimed in claim 1, wherein a sequence of OCT images in time is recorded.

15. The method as claimed in claim 1, wherein a sequence of OCT images in time is recorded, and wherein local axial spectra of step (b) are reconstructed and analyzed in time.

16. The method as claimed in claim 1, wherein a sequence of OCT images in time is recorded, and wherein time dependences of calculated information parameters for each pixel of an OCT 2D image or each voxel of a 3D OCT image are calculated and plotted.

17. The method as claimed in claim 1, wherein the radiation receiver is a 2D detector and the spectral interferograms are formed simultaneously for all image points.

18. The method as claimed in claim 1, wherein said mapping includes a map of a spatial period at a maximum signal, which is a distribution of a dominant size of the structure of the object.

* * * * *